(12) United States Patent
Emmett et al.

(10) Patent No.: US 11,305,076 B2
(45) Date of Patent: *Apr. 19, 2022

(54) METHOD FOR PROVIDING AN AEROSOL-GENERATING DEVICE, AEROSOL-GENERATING DEVICE AND FLAT AEROSOL-GENERATING ARTICLE FOR USE IN SUCH A DEVICE

(71) Applicant: PHILIP MORRIS PRODUCTS S.A., Neuchatel (CH)

(72) Inventors: Robert William Emmett, Neuchatel (CH); Tony Reevell, London (GB)

(73) Assignee: Philip Morris Products S.A., Neuchatel (CH)

( * ) Notice: Subject to any disclaimer, the term of this patent is extended or adjusted under 35 U.S.C. 154(b) by 511 days.

This patent is subject to a terminal disclaimer.

(21) Appl. No.: 16/301,285

(22) PCT Filed: May 24, 2017

(86) PCT No.: PCT/EP2017/062628
§ 371 (c)(1),
(2) Date: Nov. 13, 2018

(87) PCT Pub. No.: WO2017/202965
PCT Pub. Date: Nov. 30, 2017

(65) Prior Publication Data
US 2020/0221767 A1     Jul. 16, 2020

(30) Foreign Application Priority Data
May 25, 2016   (EP) ..................................... 16171375

(51) Int. Cl.
*A24B 3/14*      (2006.01)
*A24F 40/42*    (2020.01)
(Continued)

(52) U.S. Cl.
CPC ............... *A61M 15/06* (2013.01); *A24B 3/14* (2013.01); *A24D 1/20* (2020.01); *A24F 40/40* (2020.01);
(Continued)

(58) Field of Classification Search
CPC .................................. A24B 3/14; A24F 40/42
(Continued)

(56) References Cited

U.S. PATENT DOCUMENTS 6,234,455 B1   5/2001   Wittek
8,881,737 B2   11/2014  Alderman
(Continued)

FOREIGN PATENT DOCUMENTS

CN   103179870   6/2013
CN   109152897   1/2019
(Continued)

OTHER PUBLICATIONS

Office Action and Search Report issued in Russia for Application No. 2018143530 dated Jul. 22, 2020 (11 pages). English translation included.

(Continued)

*Primary Examiner* — Kelly M Gambetta
*Assistant Examiner* — Russell E Sparks
(74) *Attorney, Agent, or Firm* — Mueting Raasch Group

(57) ABSTRACT

The method for providing an aerosol-generating device for use with a shape-transformable aerosol-forming substrate comprises providing an aerosol-generating device comprising a device housing comprising a moulding cavity. The moulding cavity at least partially corresponds to a moulding space between a first mould half and a second mould half of a mould, the first mould half and the second mould half being internal surfaces of the device housing. The method further comprises the step of providing a flat aerosol-

(Continued)

forming substrate adapted to change shape when pressed into the moulding cavity and being transformed into a non-flat aerosol-forming substrate. The invention also refers to a flat aerosol-generating article and a kit comprising a flat aerosol-generating article and an aerosol-generating device.

13 Claims, 4 Drawing Sheets

(51) Int. Cl.

| | |
|---|---|
| *A24F 40/20* | (2020.01) |
| *A61M 15/06* | (2006.01) |
| *A24F 40/40* | (2020.01) |
| *A24F 40/50* | (2020.01) |
| *A24D 1/20* | (2020.01) |
| *A24F 40/485* | (2020.01) |
| *A24B 15/167* | (2020.01) |

(52) U.S. Cl.
CPC ............ *A24F 40/42* (2020.01); *A24F 40/485* (2020.01); *A24F 40/50* (2020.01); *A24B 15/167* (2016.11); *A24F 40/20* (2020.01)

(58) Field of Classification Search
USPC .......................................................... 131/329
See application file for complete search history.

(56) References Cited

U.S. PATENT DOCUMENTS

| | | | | |
|---|---|---|---|---|
| 9,295,286 | B2 | 3/2016 | Shin | |
| 9,532,603 | B2 | 1/2017 | Plojoux | |
| 9,999,256 | B2 * | 6/2018 | Abramov | A24F 47/008 |
| 10,188,144 | B2 * | 1/2019 | Dickens | A61M 15/06 |
| 10,271,578 | B2 * | 4/2019 | John | A24F 40/46 |
| 2009/0293888 | A1 | 12/2009 | Williams | |
| 2014/0060554 | A1 | 3/2014 | Collett | |
| 2014/0182608 | A1 | 7/2014 | Egoyants | |
| 2015/0163859 | A1 | 6/2015 | Schneider | |
| 2017/0095623 | A1 * | 4/2017 | Trzecieski | A61M 11/042 |
| 2020/0046023 | A1 | 2/2020 | Reevell | |

FOREIGN PATENT DOCUMENTS

| | | | |
|---|---|---|---|
| EP | 3166430 | A1 | 1/2016 |
| EP | 3166425 | A1 | 5/2017 |
| EP | 3166427 | A1 | 5/2017 |
| EP | 3364796 | | 8/2018 |
| GB | 2529201 | | 2/2016 |
| JP | H02-286069 | | 11/1990 |
| JP | 2015-532828 | | 9/2012 |
| JP | 2008-212205 | | 9/2018 |
| RU | 2602053 | | 11/2016 |
| WO | WO 2010/113702 | | 10/2010 |
| WO | WO 2015/114325 | | 8/2015 |
| WO | WO2015/114328 | | 8/2015 |
| WO | WO 2016/005601 | | 1/2016 |
| WO | WO 2016/050873 | | 4/2016 |

OTHER PUBLICATIONS

PCT Search Report and Written Opinion for PCT/EP2017/062628 dated Aug. 1, 2017 (11 pages).

Office Action issued in China for Application No. 201780031090.2 dated Aug. 31, 2020 (13 pages). English translation included.

Office Action issued in Japan for Application No. 2018-561535 dated Jun. 10, 2021 (5 pages). English translation included.

* cited by examiner

METHOD FOR PROVIDING AN AEROSOL-GENERATING DEVICE, AEROSOL-GENERATING DEVICE AND FLAT AEROSOL-GENERATING ARTICLE FOR USE IN SUCH A DEVICE

This application is a U.S. National Stage Application of International Application No. PCT/EP2017/062628 filed May 24, 2017, which was published in English on Nov. 30, 2017, as International Publication No. WO 2017/202965 A1. International Application No. PCT/EP2017/062628 claims priority to European Application No. 16171375.5 filed May 25, 2016.

The invention relates to a method for providing an aerosol-generating device for use with a shape-transformable aerosol-forming substrate and a flat aerosol-generating article for use in such a device. The invention also refers to a kit for an aerosol-generating system comprising an aerosol-generating device and a flat aerosol-generating article.

Various aerosol-generating devices using aerosol-forming substrate, which is heated rather than combusted are known. Aerosol-forming substrate used in such devices typically has a rod-shape imitating the shape of common smoking articles and providing a large vaporization surface. However, these substrates or articles comprising the substrates are not optimized for storing.

Thus, it would be desirable to have an aerosol-generating article, which requires little space for storing and which provides a large surface for aerosol-formation. It would also be desirable to have an aerosol-generating device adapted for use with such an article and a method to provide an aerosol-generating device for use with such an article.

Thus, according to the invention, there is provided a method for providing an aerosol-generating device for use with a shape-transformable aerosol-forming substrate. The method comprises the step of providing an aerosol-generating device comprising a device housing comprising a moulding cavity. The moulding cavity at least partially corresponds to a moulding space between a first mould half and a second mould half of a mould, wherein the first mould half and the second mould half are internal surfaces of the device housing. The method further comprises the step of providing a flat aerosol-forming substrate adapted to change shape when pressed into the moulding cavity and being transformed into a non-flat aerosol-forming substrate. The method may comprise the steps of opening the device housing, thereby opening the first and second mould halves and positioning the flat aerosol-forming substrate in between the first and second mould halves. Yet a further step may comprise closing the device housing, thereby closing the first and second mould halves, and thereby transforming the flat aerosol-forming substrate into the non-flat aerosol-forming substrate. The non-flat aerosol-forming substrate preferably has a shape corresponding to the non-flat moulding space in the mould upon closing of the mould.

A flat aerosol-forming substrate is provided, which may be easy and cost efficient to manufacture and to stack and store in a space saving manner. Individual packaging is simplified, which may keep the product longer fresh and may reduce damage during transport. In particular, the aerosol-forming substrate may be a tobacco containing aerosol-forming substrate, preferably a solid tobacco containing aerosol-forming substrate.

The transformability of the shape of the aerosol-forming substrate from a flat shape into a non-flat, for example three-dimensional geometric form, may facilitate the manufacture of small devices, preferably without reducing a total surface of or amount of aerosol-forming substrate. Due to the transformability, the flat substrate may be large and provide a large surface area for substances to be vaporized even in relatively small moulding cavities provided for receiving the aerosol-forming substrate. Preferably, the flat substrate has a dimension larger than a dimension of the device itself, for example larger than a dimension of a moulding cavity for receiving the aerosol-forming substrate or larger than a dimension of a mould. For example, the flat substrate may have a width or length or diameter, which is larger than a diameter or lateral extension of a device housing, larger than a width or length or diameter of a moulding cavity or larger than a diameter or width or length of a mould.

Preferably, the method comprises the step of providing the moulding cavity in a side and along the length of the aerosol-generating device. Thus, a portion or substantially an entire length of the device may be used to receive the aerosol-forming substrate. Such moulding cavities allow the use of flat strips of aerosol-forming substrates, which may be manufactured in a very cost efficient manner causing very low waste. The flat aerosol-forming substrates may be arranged in the moulding cavity arranged in the side and along the length of the device.

The flat substrate may basically be regarded as substantially two-dimensional, theoretically neglecting a thickness of the substrate. The term 'flat' substrate or 'flat' article is used throughout the specification to refer to a substrate or article that is in the form of a substantially two dimensional topological manifold. Thus, the flat substrate or flat article extends in two dimensions along a surface substantially more than in a third dimension. In particular, the dimensions of the flat substrate or flat article in the two dimensions within the surface is at least 5 times larger than in the third dimension, normal to the surface. An example of a flat substrate or flat article is a structure between two substantially parallel imaginary surfaces, wherein the distance between these two imaginary surfaces is substantially smaller than the extension within the surfaces. Preferably, the flat substrate or the flat article comprising the substrate is planar.

Through the transformation of the substrate upon preparing the device, the flat substrate is moulded in the mould of the device to its final non-flat shape. By the moulding process, the flat substrate is deformed and shaped to extend also into the third dimension. Thus a lateral extension of the flat substrate is reduced in favour of an extension in the third dimension. Upon closing the mould halves, the reduction of the lateral dimension of the flat substrate due to its deformation, allows the use of larger substrates than seem to fit into the mould or into the moulding cavity or even into the device, respectively.

A flat aerosol-forming substrate may have a thickness in a range between 0.2 millimeter and 6 millimeter, preferably, between 0.5 millimeter and 4 millimeter, for example between 0.2 millimeter and 2 millimeter or between 0.4 millimeter and 4 millimeter.

Throughout this application, whenever a value is mentioned, this is to be understood such that the value is explicitly disclosed. However, a value is also to be understood as not having to be exactly the particular value due to technical considerations.

The aerosol-forming substrate or aerosol-generating article comprises a flexibility such as to be transformable in a non-flat shape. Preferably, substrate and article comprise a flexibility such as to not break or be ruptured upon transformation. Preferably, transformation excludes a folding of the substrate or article onto itself. Preferably, the substrate is not bent by more than 135 degree upon moulding, more preferably by not more than 90 degree upon being moulded in the mould.

The flat substrate may be provided in the form of a single sheet of aerosol-forming substrate. In the mould of the device, a single sheet may be transformed into a three-dimensional geometrical form, for example, into a cone-like shape, an undulating corrugated sheet or a hollow or full rod or rods.

The flat aerosol-forming substrate may extend in a general plane and be transformable such that the non-flat substrate after transformation still extends along the general plane and additionally in a direction perpendicular to the general plane.

Extending along the general plane is meant that the non-flat substrate may extend exactly in the general plane but also extend substantially in the general plane, wherein parts of the substrate deviate out of the general plane in the third dimension perpendicular to the general plane.

If a thickness of the flat substrate is considered as basic extension of the flat substrate in the third dimension, then the non-flat substrate after transformation preferably extends into the third dimension by at least twice the basic dimension, for example between 2 to 5 times the basic extension. In some example the non-flat substrate may extend more than five times of the basic extension into the third dimension, for example 5 to 8 times.

The moulding of the aerosol-forming substrate upon preparing a device for use, also guarantees a very efficient heating since the aerosol-forming substrate is pressed against a heating element preferably arranged in the mould.

The method according to the invention may comprise the further step of providing the device housing with a lid portion. The device housing comprises a first internal surface and the lid portion comprises a second internal surface. The first and second internal surface form the first and second mould halves with a moulding space in the form comprising a series of concave shapes. Accordingly, the flat aerosol-forming substrate may be adapted to being transformed in the moulding space into a non-flat aerosol-forming substrate comprising a series of concave shapes. The series of concave shapes may, for example, be provided on the first mould half, on the second mould half or on both mould halves. For example the flat article may be transformed into a rippled sheet, into a corrugated sheet or into a substrate comprising a series of tubes or rods arranged in parallel. The flat aerosol-forming substrate may, for example, be adapted to being divided into a plurality of non-flat aerosol-forming sub-substrates in the moulding cavity comprising a series of concave shapes.

Forming shapes comprising a series of concave shapes facilitates the use of large flat aerosol-forming substrates having a longitudinal or lateral substrate extension, which is larger than a longitudinal or lateral extension of a mould, possibly even larger than a longitudinal or lateral extension of a moulding cavity for receiving the aerosol-forming substrate in the device. The transformed substrates may have a corrugated shape, which shape has proven to be efficient in aerosol formation and convenient in use and handling in aerosol-generating devices. The transformed substrates may, for example have a shape comprising several tubes. This shape has proven to be efficient in selective heating and aerosol formation of parts of the substrate only.

Such substrate forms may be heated in a very efficient manner, for example along an entire length or width of the substrate. Such substrate forms may also be removed from a device in a simple manner, for example not requiring a user's contact with the used substrate.

In addition, the method allows the manufacture of devices with an as such known set-up comprising mouthpiece and body portion, wherein the form of or an airflow management in the mouthpiece may be kept independent of the aerosol-generating article used in the device. Thus, a lid for opening the device providing access to the moulding cavity for receiving the aerosol-forming substrate or aerosol-generating article, respectively, may be provided in a body portion only. However, a device may, for example, be designed in one part, wherein the lid is arranged in the device housing possibly extending into or being part of a mouthpiece portion of the device.

As used herein, the term 'aerosol-generating device' is used to describe a device that is configured for interaction with an aerosol-forming substrate to generate an aerosol. The aerosol-generating device may be a hand-held device. Preferably, the aerosol-generating device is a puffing device for generating an aerosol that is directly inhalable by a user thorough the user's mouth. Most preferably, the aerosol-generating device is configured for use with an aerosol-generating article comprising an aerosol-forming substrate, in particular for use with an aerosol-generating article according to the invention and as described herein.

A heating in the device may be provided in the housing, for example in a body portion or in the lid portion. The heating may, for example, be resistive or inductive. The heating may be provided for heating the first or the second mould half. The heating may, for example, be incorporated into any of the mould halves. Preferably, the heating is provided in the device housing, preferably in a body portion of the device. One or several heating elements may be provided for heating the aerosol-forming substrate. Several heating elements may be provided for a selective, for example, an individual, preferably a sequential heating of substrate sections.

According to the invention, there is also provided an aerosol-generating device comprising a device housing comprising a moulding cavity for receiving an aerosol-forming substrate. The moulding cavity at least partially corresponds to a moulding space between a first and a second mould half of a mould. The first mould half and the second mould half are internal surfaces of the device housing. In an open state of the mould, which open state corresponds to an open device housing, the aerosol-generating device is adapted to receive a flat aerosol-forming substrate in between the first and second mould halves. In a closed state of the mould, which closed state corresponds to a closed device housing, the moulding space in between the first and second mould halves has a non-flat shape.

The first mould half and the second mould half may have corresponding shapes, for example the internal surfaces of the device housing may be formed such that a first mould half may be a cavity and a second mould half may be a correspondingly formed protrusion or vice versa. First and second mould halves may also have the same shape. For example the first mould half may be a cavity and the second mould half may be a cavity as well.

The first and second mould halves are adapted to transform a flat aerosol-forming substrate supplied between the first and second mould halves into a non-flat aerosol-forming substrate having a shape corresponding to the non-flat moulding space in the mould upon closing of the mould, which is preferably directly correlated with a closing of the device housing.

One of the first or second mould halves may comprise a heating element for heating the transformed non-flat aerosol-forming substrate.

The device housing may comprise a moulding cavity for receiving an aerosol-forming substrate. The moulding cavity may be arranged in a side and along the length of the aerosol-generating device. The device housing may further comprise a lid portion providing access to the moulding cavity.

The first mould half forms a first internal surface of a lid portion and a second mould half forms a second internal surface of the device housing. In a closed position of the lid portion the mould is in a closed state forming a non-flat moulding space in between the mould halves. The first and second mould halves are adapted to transform a flat aerosol-forming substrate supplied between the first and second mould halves into a non-flat aerosol-forming substrate having a shape corresponding to the non-flat moulding space upon closing of the lid portion.

At least one of the first or second mould half may comprise a series of concave shapes. The first and the second mould haves may comprise a series of concave shapes. The first and the second mould half may comprise corresponding undulating shapes. The first and second mould haves may be formed such that the flat aerosol-forming substrate is transformed, for example, into a rippled sheet, a corrugated sheet or into a series of rods arranged in parallel upon closing of the lid of the body portion. The tubular regions may be pinched off during moulding such as to form individual tubes allowing individual airflows to pass through the tubes. The substrate may remain a single unit with a common airflow through the entire substrate.

The series of concave shapes may be arranged parallel or perpendicular to a longitudinal axis of the device housing.

If a flat aerosol-forming substrate is transformed into a series of tubes or rods, preferably the longitudinal axis of the rods are parallel to a longitudinal axis of the moulding cavity and parallel to a longitudinal axis of the device housing.

If a flat aerosol-forming substrate is transformed into a rippled or an undulating sheet, preferably the ripples and undulations of the sheet are perpendicular to the longitudinal axis of the device housing.

Further aspects of the device have been described relating to the method according to the invention and will not be repeated.

An airflow channel may be provided through the moulding cavity, preferably, along a longitudinal direction of the device housing, in particular along a longitudinal extension of the moulding cavity. The airflow channel may be provided to pass through the mould, for example between the first and second mould half. The airflow channel may be provided to pass through the mould only.

A plurality of airflow channels may be provided through the moulding cavity, in particular through the mould.

Airflow channels may, for example, be realized by providing a mould half more narrow than the other mould half. A space between the more narrow mould half and a cavity wall may then serve as airflow channel. Airflow channels may, for example, be realized by providing a mould half with ribs. The ribs may, for example, be arranged in a longitudinal direction of the moulding cavity. A space between ribs may then serve as airflow channel though the mould. Such an embodiment allows enhanced airflow through a mould and keeping corresponding mould halves at a same size.

Each airflow channel of a plurality of airflow channels may have an air inlet provided with a valve for opening and closing each of the airflow channels of the plurality of airflow channels. Preferably, each air inlet of each of the airflow channels of the plurality of airflow channels may be opened and closed individually. Individual airflow channels may, for example be provided to let air or aerosol pass through a portion only of the aerosol-forming substrate, for example through an individual tube or rod of a series of tubes or rods.

In the aerosol-generating device an internal surface forming a mould half may be provided with a plurality of openings. The plurality of openings enables aerosol to leave the mould through the internal surface of the mould half provided with the plurality of openings. The plurality of openings may be provided in the form of, for example, micro-perforations or a porous material. The plurality of openings in an internal surface forming a mould half may substantially be the only path for an aerosol formed by heating the substrate in the mould to leave the mould and an airflow to pass through the mould. However, additional air-flow channels may be arranged in the mould or in a moulding cavity comprising the mould to let air into the mould or moulding cavity and let aerosol and air leave the mould.

One or several airflow channels or open mould surfaces may be provided to let an airflow pass through the mould or moulding cavity. However, one or several airflow channels or open mould surfaces may also be provided to enhance an airflow over an aerosol-forming substrate to enlarge a space or enable a sufficient amount of aerosol to be released into an airflow path for being transported downstream in the device.

The aerosol-generating device may comprise alignment elements for aligning an aerosol-forming substrate in the moulding cavity or in the mould, respectively.

The device may be provided with closure elements, allowing a secure opening and closing of the lid. The lid may, for example be connected to the device housing by a hinge and the lid and housing may comprise fastener, for example form fit, clamp, magnetic fastener or snap fit.

As used herein, the term 'aerosol-forming substrate' refers to a substrate that is capable of releasing volatile substances to form an inhalable aerosol therefrom. The aerosol-forming substrate may comprise a tobacco-containing material containing volatile tobacco flavour compounds, which are released from the substrate upon heating. In particular, the aerosol-forming substrate may be a tobacco containing aerosol-forming substrate, preferably a solid tobacco containing aerosol-forming substrate. Alternatively, the aerosol-forming substrate may comprise a non-tobacco material. The aerosol-forming substrate may further comprise an aerosol former. Examples of suitable aerosol formers are glycerine and propylene glycol.

The aerosol-forming substrate may comprise, for example, one or more of: powder, granules, pellets, shreds, spaghetti strands, strips or sheets containing one or more of: herb leaf, tobacco leaf, fragments of tobacco ribs, reconstituted tobacco, homogenised tobacco, extruded tobacco and expanded tobacco.

Optionally, the aerosol-forming substrate may contain additional tobacco or non-tobacco volatile flavour compounds, to be released upon heating of the aerosol-forming substrate. The aerosol-forming substrate may also contain micro-capsules that, for example, include the additional tobacco or non-tobacco volatile flavour compounds and such micro-capsules may melt during heating of the solid aerosol-forming substrate.

The aerosol-forming substrate may comprise a sheet of homogenised tobacco material that has been formed or cut into a desired shape of flat piece of aerosol-forming substrate.

The aerosol-forming substrate may be substantially disc shaped. The aerosol-forming substrate may be substantially rectangular.

Tobacco containing slurry and a tobacco sheet forming the aerosol-forming substrate made from the tobacco containing slurry comprises tobacco particles, fiber particles, aerosol former, binder and for example also flavours.

Preferably, the aerosol-forming tobacco substrate is a tobacco sheet comprising tobacco material, fibers, binder and aerosol former. Preferably, the tobacco sheet is a cast leaf. Cast leaf is a form of reconstituted tobacco that is formed from a slurry including tobacco particles, fiber particles, aerosol former, binder and for example also flavours.

Tobacco particles may be of the form of a tobacco dust having particles in the order of 30 micrometers to 250 micrometers, preferably in the order of 30 micrometers to 80 micrometers or 100 micrometers to 250 micrometers, depending on a desired sheet thickness and casting gap, where the casting gap typically defines the thickness of the sheet, preferably corresponding to the thickness of the aerosol-generating article or half of the thickness of the aerosol-generating article in case of a folded article.

Fiber particles may include tobacco stem materials, stalks or other tobacco plant material, and other cellulose-based fibers such as wood fibers having a low lignin content. Fiber particles may be selected based on the desire to produce a sufficient tensile strength for the sheet versus a low inclusion rate, for example, an inclusion rate between approximately 2 percent to 15 percent. Alternatively, fibers, such as vegetable fibers, may be used either with the above fiber particles or in the alternative, including hemp and bamboo.

Aerosol formers included in the slurry for forming the cast leaf may be chosen based on one or more characteristics. Functionally, the aerosol former provides a mechanism that allows it to be volatilized and convey nicotine or flavouring or both in an aerosol when heated above the specific volatilization temperature of the aerosol former. Different aerosol formers typically vaporize at different temperatures. An aerosol former may be chosen based on its ability, for example, to remain stable at or around room temperature but able to volatize at a higher temperature, for example, between 40 degree Celsius and 450 degree Celsius. The aerosol former may also have humectant type properties that help maintain a desirable level of moisture in an aerosol-forming substrate when the substrate is composed of a tobacco-based product including tobacco particles. In particular, some aerosol formers are hygroscopic material that function as a humectant, that is, a material that helps keep a substrate containing the humectant moist.

One or more aerosol former may be combined to take advantage of one or more properties of the combined aerosol formers. For example, triacetin may be combined with glycerol and water to take advantage of the triacetin's ability to convey active components and the humectant properties of the glycerol.

Aerosol formers may be selected from the polyols, glycol ethers, polyol ester, esters, and fatty acids and may comprise one or more of the following compounds: glycerol, erythritol, 1,3-butylene glycol, tetraethylene glycol, triethylene glycol, triethyl citrate, propylene carbonate, ethyl laurate, triacetin, meso-Erythritol, a diacetin mixture, a diethyl suberate, triethyl citrate, benzyl benzoate, benzyl phenyl acetate, ethyl vanillate, tributyrin, lauryl acetate, lauric acid, myristic acid, and propylene glycol.

The aerosol-forming substrate or the aerosol-forming slurry forming the substrate may contain waxes or fats, which waxes or fats are added for a low temperature release of aerosol-forming substances from the solid aerosol-forming substrate. Some waxes and fats are known for their ability to lower the temperature where an aerosol former is released from a solid substrate containing said waxes or fats.

Preferably, tobacco containing slurry comprises homogenized tobacco material and comprises glycerol or propylene glycol as aerosol former. Preferably, the aerosol-forming substrate is made of a tobacco containing slurry as described above.

According to the invention, there is further provided a flat aerosol-generating article for use in an aerosol-generating device, in particular for use with an aerosol-generating device according to the invention and as described herein. The flat aerosol-generating article comprises a layered structure comprising at least one layer comprising aerosol-forming substrate. The article further comprises an open layer adapted for aerosol to flow within the layer.

In particular, the aerosol-forming substrate may be a tobacco containing aerosol-forming substrate, preferably a solid tobacco containing aerosol-forming substrate.

An open layer may be a porous layer. Preferably, the open layer comprises a predefined general flow direction for the aerosol and possibly an airflow to flow in the layer. Preferably aerosol is made to flow along a longitudinal, a radial or in a central direction of the article. Preferably, aerosol evaporated from the aerosol-forming substrate layer flows in the open layer and follows the contour of the substrate layer. A predefined general flow direction of the open layer may lead gaseous fluid, typically aerosol, air, evaporated substances or aerosol-containing air into the direction of an outlet of an aerosol-generating device, for example into the direction of a mouthpiece or an outlet opening of the device. An open layer may, for example, be made of a foam or cellulose type material comprising an open cell structure.

The open layer allows aerosol to pass through the article also after transformation into a non-flat shape.

The open layer preferably does not comprise an aerosol-forming substrate, in particular does not comprise tobacco. That is, the open layer preferably is a non-aerosol-forming open layer or an open layer free of aerosol-forming substrate, in particular a tobacco-free open layer. Likewise, the open layer preferably is not made of an aerosol-forming substrate, in particular not made of tobacco.

A further layer of the layered structure may be a protective layer covering the at least one layer comprising the aerosol-forming substrate. A protective layer may be pervious to substances evaporated from the substrate and is typically not removed before use of the article. Protective layers may, for example, be paper layers such as cigarette paper, in the form of a top and a bottom layer of the flat aerosol-generating article.

The layered structure may comprise an additional aerosol-forming substrate layer.

The flat article facilitates stacking of the article and simplifies storing and transport of the article. The flat aerosol-generating article or a stack of aerosol-generating articles may be enveloped with a packaging, which is removed before use of the article(s).

The flat aerosol-generating article is transformable into a non-flat shape, preferably into a corrugated shape or a shape comprising at least partial rod shapes. Such partial rod shapes preferably have round forms such as concave or convex sides, circular or elliptical cross sections but may also have angled shapes such as rectangular sides or rectangular cross sections. Preferred non-flat shapes of the article are undulating sheets, sheets provided with ripples or a sheet formed into series of tubes or rods connected or disconnected from each other.

Preferably, the flat article has the shape of a rectangle. A rectangular flat article may, for example, have a length in a range between 30 millimeter and 100 millimeter, preferably between 40 millimeter and 80 millimeter and have a width in a range between 5 millimeter and 40 millimeter, preferably between 10 millimeter and 20 millimeter.

An aerosol-generating system may comprise an aerosol-generating device comprising a device housing according to the invention and as described herein. The system further comprises a shape-transformable aerosol-generating article. In a preparation state of the system the transformable aerosol-generating article comprises a flat aerosol-forming substrate. In a ready to be used state of the system the system comprises a non-flat aerosol-generating article comprising a non-flat aerosol-forming substrate transformed through deformation of the flat aerosol-generating article between device housing parts forming first and second mould halves. Preferably, by assembling the device housing parts the first and second mould halves are closed and the substrate is moulded. The shape-transformable aerosol-generating article may be a flat aerosol-generating article according to the invention and as described herein but may also be a single sheet of aerosol-forming substrate.

According to the invention, there is yet further provided a kit for an aerosol-generating system. The kit comprises an aerosol-generating device comprising a device housing comprising a moulding cavity. The moulding cavity at least partially corresponds to a moulding space between a first and a second mould half of a mould. The first mould half and the second mould half are internal surfaces of the device housing. The mould has a longitudinal mould extension and a lateral mould extension. The kit further comprises a flat aerosol-generating article comprising a flat aerosol-forming substrate having a longitudinal substrate extension and a lateral substrate extension. The flat aerosol-generating article is configured to be mounted in the moulding cavity in between the first and second mould half of the device housing, and is configured to be transformed into a non-flat aerosol-forming substrate. Therein the lateral substrate extension is larger than the lateral mould extension or the longitudinal substrate extension is larger than the longitudinal mould extension. The non-flat aerosol-forming substrate preferably has a shape corresponding to the non-flat moulding space in the mould upon closing of the mould.

A longitudinal mould extension is seen in longitudinal direction of the device and the lateral mould extension is seen in lateral direction of the device.

An aerosol-forming substrate may, for example, have a substantially rectangular form and be adapted to be inserted into a moulding cavity of the device housing. Through the moulding process between the moulds, a length or a width or a length and a width of the substrate is thereby reduced such that the original length or width or length and width of the substrate may be larger than a length or width of the mould. Preferably, in these embodiments, the substrate is not larger than a moulding cavity for constructional reasons of a device.

Preferably, the moulding cavity is arranged in a side and along the length of the device housing.

The device may comprise a mouthpiece portion and a body portion. Preferably, the moulding cavity is arranged in the body portion comprising a lid portion.

Preferably, the aerosol-forming substrate has a rectangular shape. Preferably, the rectangular substrate has a length longer than a length of the mould or has a width larger than a width of the mould. Preferably, the length of the rectangular substrate is shorter than a longitudinal extension of the moulding cavity for receiving the aerosol-generating article. Preferably, the width of the rectangular substrate is smaller than the width of the moulding cavity for receiving the aerosol-generating article.

A length of an aerosol-forming substrate may, for example, be up to 40 percent longer than a length of the moulding cavity. Preferably, a length of a moulding cavity may be up to 20 percent longer or, more preferably, up to 10 percent longer than the length of a moulding cavity.

A width of an aerosol-forming substrate may, for example, be 5 percent to 20 percent wider than a width of a moulding cavity, preferably 5 percent to 15 percent.

The aerosol-generating device of the kit may be an aerosol-generating device according to the invention and as described herein.

The aerosol-generating article of the kit may be an aerosol-generating article according to the invention and as described herein.

In particular, the aerosol-forming substrate may be a tobacco containing aerosol-forming substrate, preferably a solid tobacco containing aerosol-forming substrate.

The invention is further described with regard to embodiments, which are illustrated by means of the following drawings, wherein.

Figures 1, 2:
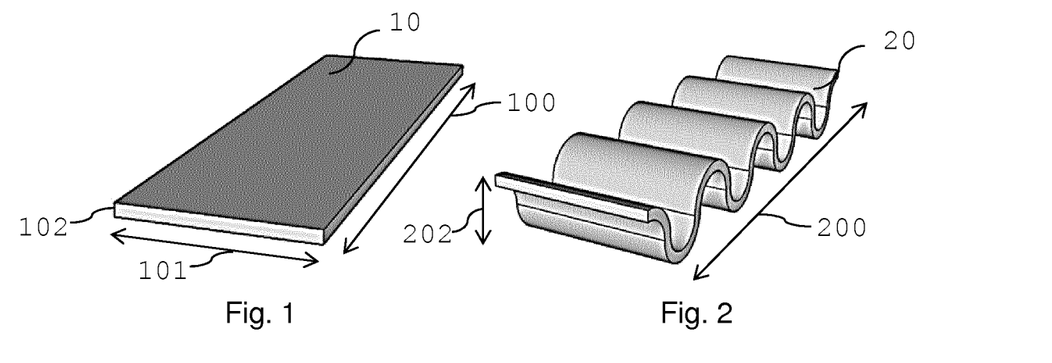
FIG. 1 shows a flat rectangular-shaped aerosol-forming substrate.
FIG. 2 shows the shape-transformed substrate of FIG. 1 as undulating sheet.

The flat aerosol-generating article shown in FIG. 1 is a strip 10 of an aerosol-forming substrate, preferably a rectangle cut from a tobacco containing cast leaf. The rectangle may, for example, have a length 100 of 80 mm and a width 101 of 20 mm. A thickness 202 of the strip may be in a range between 0.5 mm and 2 mm.

In the mould of a corresponding aerosol-generating device, the flat strip 10 may be transformed into a non-flat article having an extension in the direction perpendicular to the plane of the flat article, which perpendicular extension is preferably several times larger than the thickness 102 of the flat article.

The flat strip 10 may, for example, be transformed into a corrugated sheet 20 a shown in FIG. 2. The undulating sheet comprises a series of undulations. The height 202 of the corrugated sheet 20 is about 5 to 10 times larger than the thickness of the flat strip 10. Due to the transforming of the strip 10, the length 200 of the corrugated sheet 20 is shorter than the length 202 of the flat strip 10, for example by at least 20 percent.

Figure 3:
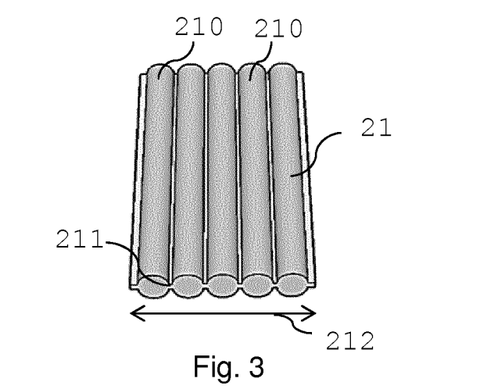
FIG. 3 shows a shape-transformed substrate in the form of a series of rods.

The strip 10 may also be formed into a series of rods 21. The individual rods 210 are arranged in parallel and along the length of the article as shown in FIG. 3. The rods 21 may be connected to each other by bonding bridges 211 and form a single article. The rods 210 may also completely be separated upon moulding and form individual sub-sub-strates.

Upon moulding of the flat strip 10 into a series of rods 21, the material for the diameter of the rods may be partially taken from the original thickness 102 of the strip 10 and partially from the width 101 of the strip 10. Thus, the width 212 of the series of rods 21 is slightly smaller than the width 101 of the strip 10.

Figure 4:
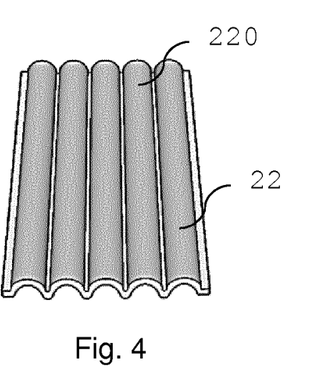
FIG. 4 shows a shape-transformed substrate in the form of a rippled sheet.

The rectangle 10 may also be provided with ripples 22 as shown in FIG. 4. The individual ripples 220 form a series of tunnels arranged in parallel and along the length of the article.

Figure 5:
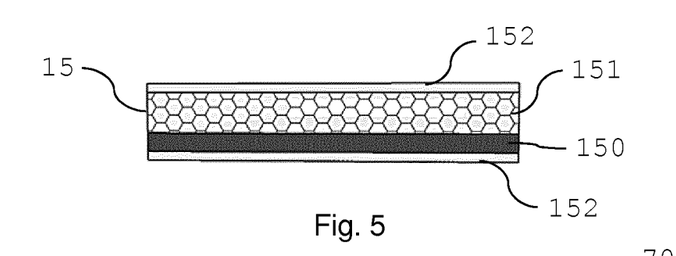
FIG. 5 shows a cross-section of an open, layered aerosol-forming substrate.

FIG. 5 shows the cross section of an open, layered flat aerosol-generating article The article comprises a layer 150 of an aerosol-forming substrate, preferably a layer of a tobacco containing cast leaf. A second layer 151 is an open layer, for example a mesh arrangement. The open layer 151 allows air and aerosol or evaporated substances from the substrate 150 to enter inside the aerosol-generating article and into the open layer 151 also after the substrate has been transformed into a non-flat article. The article is provided with outer paper layers 152, for example cigarette paper, provided on top of the open layer 151 and below the aerosol-forming substrate layer 150. A thickness of the article may be in a range between 2 mm and 5 mm.

Preferably, a thickness of the paper layers 152 is each between 0.05 mm and 0.2 mm.

Preferably, a thickness of the aerosol-forming substrate layer 150 is between 0.5 mm and 2 mm.

Preferably, a thickness of the open layer 151 is between 1.5 mm and 3 mm.

Preferably, a thickness of the open article 15 is the same as a thickness of a single sheet of aerosol-forming substrate as for example shown in FIG. 1.

Figure 6:
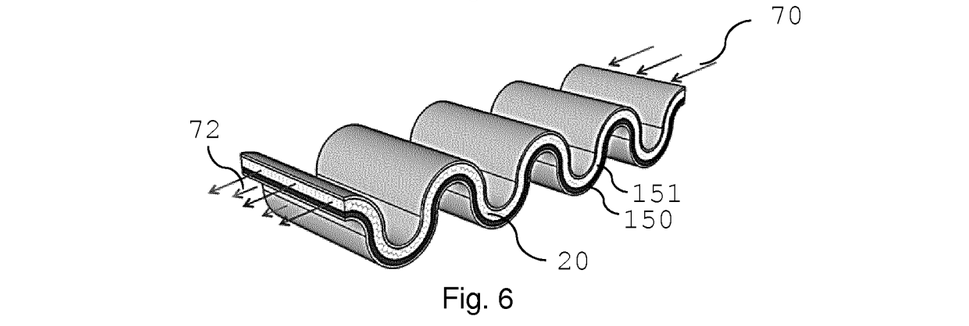
FIG. 6 shows the shape-transformed substrate of FIG. 5 as undulating sheet.

FIG. 6 shows a corrugated sheet 20 made of an open aerosol-generating article 15 as shown in FIG. 5. An airflow 70 enters the article 15 at one short end, passes along the open layer 151 inside the article and along the length of the article 15. During this transport substances or aerosol (indicated by short arrows) evaporated from the heated layer of aerosol-forming substrate 150 is picked up by the airflow and the mixed gas flow 72 leaves the article at the opposite short end of the article 15.

Figure 7:
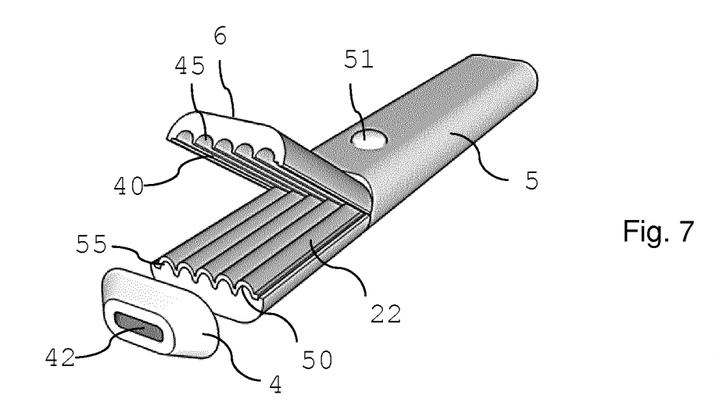
FIG. 7 shows an aerosol-generating device with rippled sheet.

FIG. 7 shows an aerosol-generating device. The device comprises a mouthpiece portion 4 comprising an outlet opening 42 and a body portion 5. The device is elongate having a flat elliptical cross section. The body portion 5 of the device may, for example, comprise a power source such as a battery and electronics for controlling a heating of the device. The body portion is also provided with an activation knob 51 for activating the device, for example starting a heating.

In FIG. 7 the body portion 5 comprises a lid 6 which is hingedly connected to the body portion 5 and provides an opening of the body portion. By opening the lid 6, access to a moulding cavity in the body portion 5 for providing an aerosol-generating article is provided.

An internal surface of the body portion 5 forms a first mould half 50. An internal surface of the lid 6 forms a second mould half 40. First and second mould halves 40, 50 correspond to each other and are formed as a series of longitudinally arranged ripples. The first mould half 50 comprises a series of protruding ripples 55 and the second mould half 40 comprises a series of corresponding inverse or recessed ripples 45.

When the lid 6 is closed, a flat sheet, for example as shown in FIG. 1, is moulded into a rippled article 22 in the moulding cavity between the ripple-shaped first and second mould haves 40, 50.

Preferably, the first mould half 50 comprises one or several heating elements for heating the rippled article 22. Preferably, one heating element is provided per longitudinal rib 55.

Figure 8:
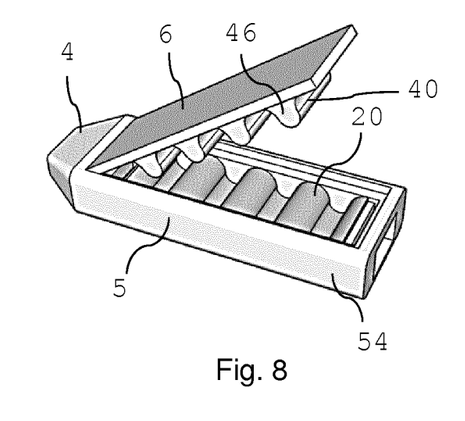
FIGS. 8,9 show an aerosol-generating device with undulating sheet.
Figure 9:
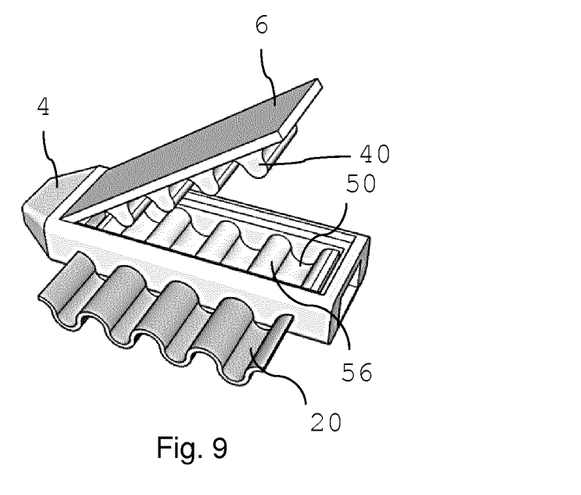

In FIG. 8 and FIG. 9 an aerosol-generating device for moulding a corrugated sheet 20 from a flat strip is shown. The body portion 5 of the device has the form of a box 54 comprising a lid 6. The lid 6 basically forms the top of the box 54. The moulding cavity for receiving the flat aerosol-generating article basically extends over the entire length and width of the box 54. The internal surface of the lid 6 is provided with a series of perpendicularly arranged undulations 46 forming the second mould half 40. The internal surface of the box 54 is provided with corresponding undulations 56 forming the first mould half 50.

Figure 10:
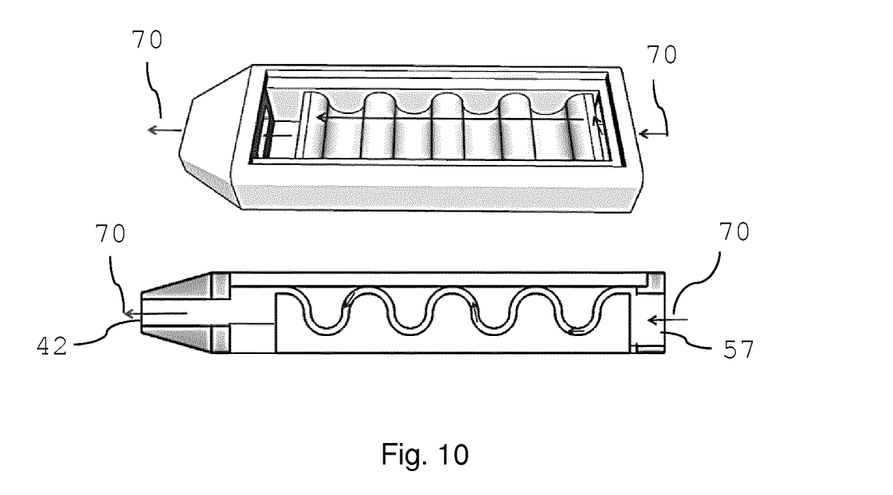
FIG. 10 illustrates an airflow through the device of FIGS. 8 and 9.

In FIG. 10 an airflow 70 through the device of FIG. 8 and FIG. 10 is shown. Such an airflow enters the distal end 57 of the device undulates through the moulding space formed between the first and second mould haves 40, 50 and leaves the device through the outlet opening 42 in the mouthpiece 4. If an aerosol-forming substrate, for example a cast leaf is provided in the moulding space, evaporated substances from the heated substrate may have difficulty to be transported out of the moulding cavity, in particular if dense substrates are provided. To improve aerosol transport in the mould or in the moulding cavity, articles having an open layer as described and shown in FIGS. 5 and 6 may be used. Alternatively or in addition, at least a moulding surface may be provided as an open surface.

Figure 11:
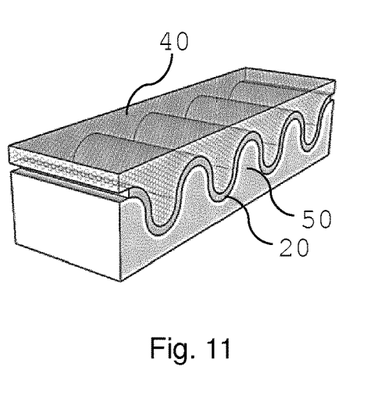
FIGS. 11,12 illustrate an embodiment of a mould comprising an undulating moulding cavity and airflow through the cavity.
Figure 12:
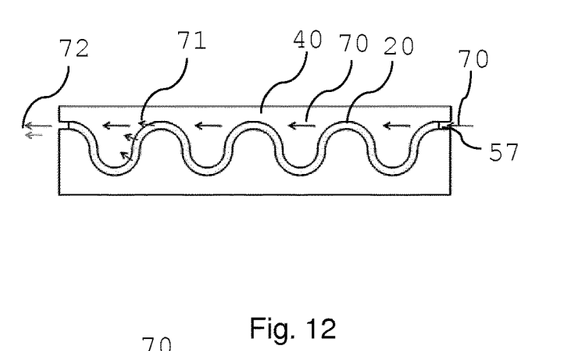

In FIG. 11 and FIG. 12, the second mould half 40 is provided as an open mould half allowing air and aerosol to pass into and through the mould half 40. Preferably, the open mould half is open into the direction of a mouthpiece or an outlet in general but does not allow aerosol to leave the mould half in another direction, for example out of a device other than out of the designated outlet. FIG. 12 shows an airflow 70 to enter the mould at inlet 57 and pass through the open mould half 40. Aerosol 71 evaporated from the substrate 20 provided in the moulding space may penetrate into the second mould half 40 and may leave the device as a mixed gas stream 72 comprising air and aerosol. The second mould half 40 may comprise open-pores material or a porous mould surface allowing aerosol or air to enter the mould half.

Figures 13, 14:
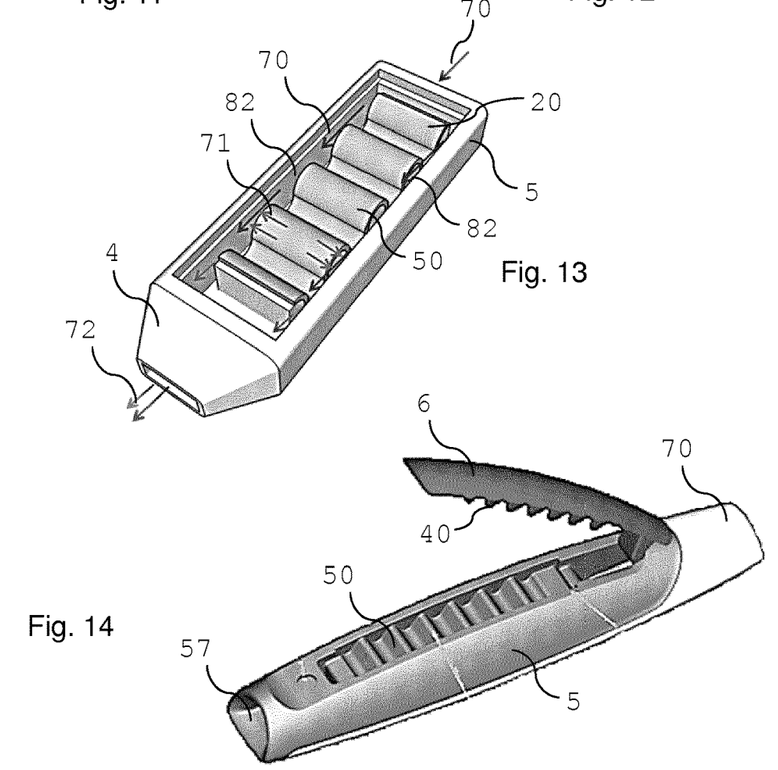
FIG. 13 illustrates another embodiment of a mould comprising an undulating moulding cavity and airflow through the cavity.
FIGS. 14,15 illustrate a further embodiment of a device comprising an undulating moulding cavity and airflow through the cavity.

FIG. 13 shows another example of facilitating an airflow through a device. In FIG. 13 the device is shown without lid. The first mould half 50 is smaller than the cavity in the device body 5. Thus, between first mould half 50 and device body side walls longitudinally running channels 82 are formed. Evaporated substances 71 do not have to pass along the entire length of the corrugated sheet 20. They may leave the substrate 20 and the mould in a sideway direction, then pass into and along the channels 82 to the mouthpiece 4.

Figure 15:
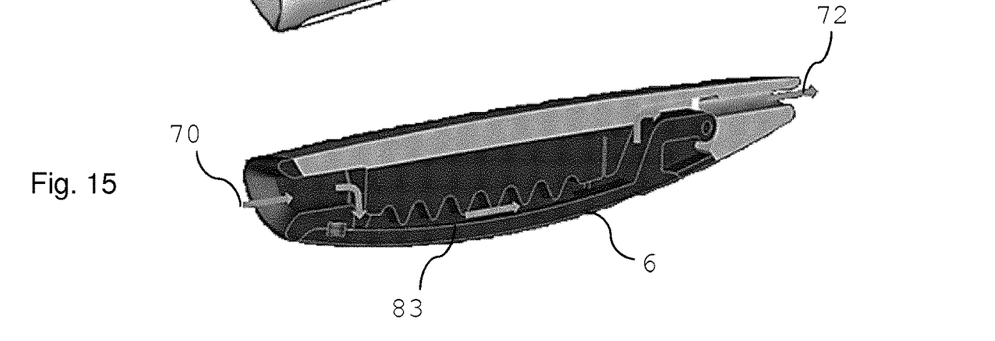

FIG. 14 and FIG. 15 (showing the device upside down) show yet another example of supporting an airflow through a device, in particular through a mould. In FIGS. 14 and 15 the cavity is longer than the mould and the width of the mould corresponds to the width of the moulding cavity. However, the second mould half 40 of the lid 6 has a width which is smaller than the width of the first mould half 50. Thus, first and second mould halves may mould a flat article into a corrugated sheet. However, along the lateral sides of the corrugated sheet airflow channels 83 are formed in the mould. An airflow 70 entering the device though an inlet opening 57 may pass through the mould along the laterally arranged channels 83 and leave the device carrying aerosol 72 generated in the device.

Figure 16:
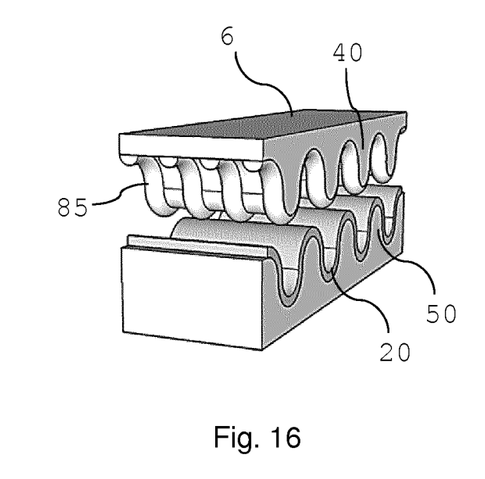
FIGS. 16,17 are perspective views of a moulding cavity comprising structured internal surfaces.
Figure 17:
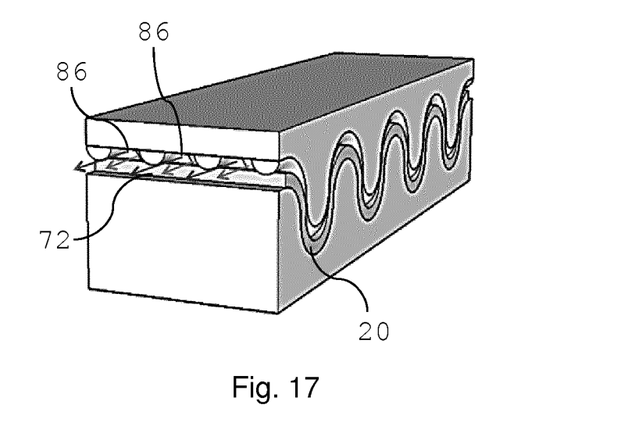

FIG. 16 and FIG. 17 are a further example of providing an airflow through a mould. In this example, one mould half 40 is provided with longitudinally running ribs 85. The undulations of the first and second mould half 40, 50 form a corrugated sheet 20 of a flat substrate. However, the distance between the ribs is not completely filled with aerosol-forming substrate. Thus, in between the ribs 85 a plurality of longitudinally running channels 86 are formed. The ribs 85 and the channels 86, accordingly, are regularly arranged over the width of the mould. Thus, a homogeneous transport of evaporated substance may be provided over the width of the corrugated sheet 20.

Figure 18:
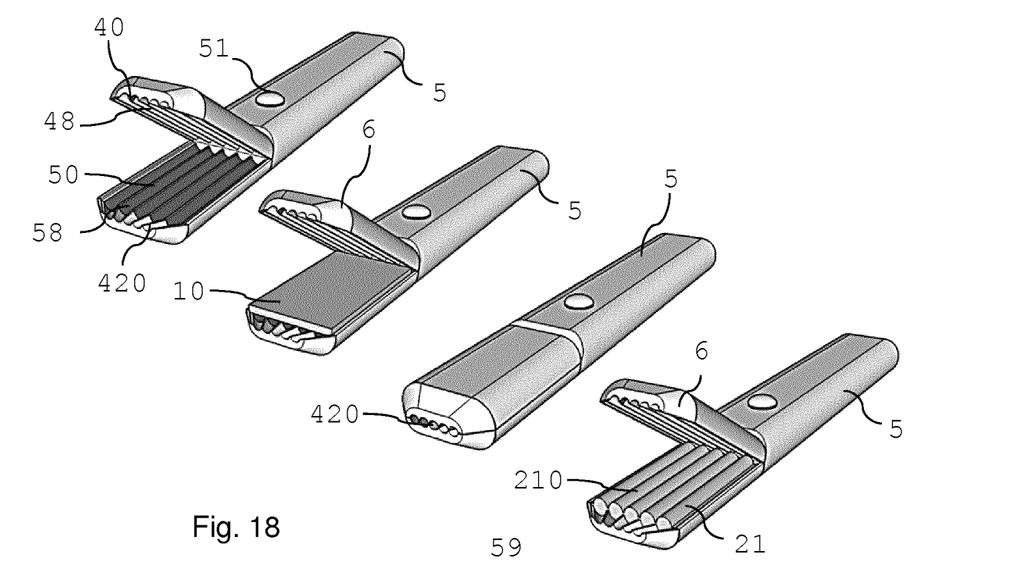
FIG. 18 illustrates an aerosol-generating device and a moulding process of a rectangular substrate sheet into a series of rods.

FIG. 18 shows an aerosol-generating device and a moulding process of a flat sheet 10 into a series of rods 21. The device comprises a body portion 5 with integrated mouthpiece 4. The device is elongate having a flat elliptical cross section. The body portion 5 of the device may, for example, comprise a power source such as a battery and electronics for controlling a heating of the device. The body portion is also provided with an activation knob 51 for activating the device, for example starting a heating.

In FIG. 18 the body portion 5 comprises a lid 6 which is hingedly connected to the body portion 5 and provides an opening of the body portion. By opening the lid, access to a moulding cavity in the body portion 5 for providing the sheet 10 is provided. The proximal end of the lid 6 comprises half of the mouthpiece 4 and the proximal end of the body portion 5 comprises the other half of the mouthpiece 4.

An internal surface of the body portion 5 forms a first mould half 50. An internal surface of the lid 6 forms a second mould half 40. First and second mould halves 40, 50 correspond to each other and are formed as a series of longitudinally arranged flutes 58, 48.

When the lid 6 is closed, each corresponding flute of the lid 6 and the body portion 5 form an individual channel and the flat sheet 10 is moulded into a series of rods 21 in the moulding cavity between the flutes 48, 58 of the first and second mould haves 40, 50. Each channel is provided with its own outlet 420. However, also a common outlet may be provided.

The first mould half 50 is provided with one or several heating elements for heating the rods 210 of the article 21. Preferably, one heating element is provided per rod 210 such that each rod may be heated individually.

In order to provide an individual airflow through each of the rods, each channel may be provided with an inlet opening 481. The inlet openings 481 may be provided with a flap 59 serving as valve as may be seen in FIG. 19. During non-use the flaps 59 are closed.

Figure 19:
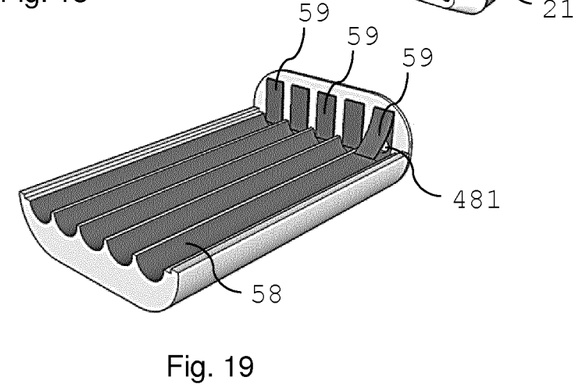
FIG. 19 shows a mould half comprising air inlet valves.

The valve function may be realised by arranging the openings 481 in a thermally conductive material or layer in thermal contact with the heating element of the flutes 58. The flaps 59 may be constructed of a bimetallic strip. As the strip is heated, the metals expand at different rates causing the strip to bend. Thus, the opening 481 covered by the respective flap 59 is opened. Preferably, the heating element provides the heating energy to activate the flap 59. A time delay in heating the flap 59 and opening the bi-metallic valve may correspond to a warm-up time of an aerosol-generating device. If an aerosol-forming substrate shall be pre-warmed, such heat may be used to open a valve. Preferably, each flap 59 may be opened individually.

The invention claimed is:

1. An aerosol-generating device comprising a device housing comprising a moulding cavity for receiving a solid tobacco containing aerosol-forming substrate,
   the moulding cavity at least partially corresponds to a moulding space between a first and a second mould half of a mould, the first mould half and the second mould half being internal surfaces of the device housing,
   wherein in an open state of the mould corresponding to an open device housing, the aerosol-generating device is adapted to receive a flat aerosol-forming substrate in between the first and second mould halves,
   wherein in a closed state of the mould corresponding to a closed device housing, the moulding space in between the first and second mould halves has a non-flat shape,
   wherein the first and second mould halves are adapted to transform a flat aerosol-forming substrate supplied between the first and second mould halves into a non-flat aerosol-forming substrate having a shape corresponding to the non-flat moulding space in the mould upon closing of the mould.

2. The aerosol-generating device according to claim 1, wherein the cavity is arranged in a side and along a length of the aerosol-generating device,
   wherein the device housing comprises a lid portion,
   wherein the first mould half forms a first internal surface of the lid portion, and a second mould half forms a second internal surface of the device housing,
   wherein in a closed position of the lid portion the mould is in a closed state forming a non-flat moulding space in between the mould halves,
   and wherein the first and second mould halves are adapted to transform the flat aerosol-forming substrate supplied between the first and second mould halves into the non-flat aerosol-forming substrate having a shape corresponding to the non-flat moulding space upon closing of the lid portion.

3. The aerosol-generating device according to claim 1, wherein at least one of the first or second mould halves comprises a series of concave shapes.

4. The aerosol-generating device according to claim 3, wherein the first and the second mould halves comprise corresponding undulating shapes.

5. The aerosol-generating device according to claim 1, wherein an airflow channel is provided through the cavity along a longitudinal direction of the device housing.

6. The aerosol-generating device according to claim 5, wherein a plurality of airflow channels are provided through the cavity, each airflow channel having an air inlet provided with a valve for opening and closing each of the airflow channels of the plurality of airflow channels.

7. The aerosol-generating device according to claim 1, wherein an internal surface forming a mould half is provided with a plurality of openings enabling aerosol to leave the mould through the internal surface of the mould half provided with the plurality of openings.

8. A kit for an aerosol-generating system, the kit comprising:
the aerosol-generating device according to claim 1, the mould having a longitudinal mould extension and a lateral mould extension;
the flat aerosol-generating article comprising a flat aerosol-forming substrate having a longitudinal substrate extension and a lateral substrate extension,
wherein the flat aerosol-generating article is configured to be mounted in the moulding cavity in between the first and second mould halves of the device housing, and is configured to be transformed into the non-flat aerosol-forming substrate having the shape corresponding to the non-flat moulding space in the mould upon closing of the mould, and wherein the lateral substrate extension is larger than the lateral mould extension or wherein the longitudinal substrate extension is larger than the longitudinal mould extension.

9. The kit according to claim 8, wherein the aerosol-forming substrate has a rectangular shape having a length longer than a length of the mould or having a width larger than a width of the mould.

10. A method for using the aerosol-generating device of claim 1 for use with a shape-transformable aerosol-forming substrate, the method comprising the steps of:
providing the aerosol-generating device comprising the device housing comprising the moulding cavity, the moulding cavity at least partially corresponding to the moulding space between the first mould half and the second mould half of the mode, the first mould half and the second mould half being internal surfaces of the device housing;
opening the device housing, thereby opening the first and second mould halves;
providing the flat aerosol-forming substrate adapted to change shape when pressed into the moulding cavity and being transformed into a non-flat aerosol-forming substrate having the shape corresponding to the non-flat moulding space in the mould upon closing of the mould.

11. The method according to claim 10, further comprising the step of providing the moulding cavity in a side and along the length of the aerosol-generating device, wherein the flat aerosol-forming substrate adapted to being transformed into the non-flat aerosol-forming substrate extends in a general plane such that the non-flat article after transformation extends along the general plane and additionally in a direction perpendicular to the general plane.

12. The method according to claim 10 comprising the steps of:
providing the device housing with a lid portion, the device housing comprising a first internal surface, the lid portion comprising a second internal surface,
the first and second internal surface forming the first and second mould halves with the moulding space in the form comprising a series of concave shapes, wherein the flat aerosol-forming substrate is adapted to being transformed in the moulding space into a non-flat aerosol-forming substrate comprising a series of concave shapes.

13. The method according to claim 10, wherein the non-flat aerosol-forming substrate is adapted to being divided into a plurality of non-flat aerosol-forming sub-substrates.

* * * * *